7/28/87 OR 4,682,856

United States Patent [19]

Holdridge

[11] Patent Number: 4,682,856

[45] Date of Patent: Jul. 28, 1987

[54] CONTOURED TRANSPARENCY PROVIDING REDUCED OPTICAL DISTORTION AND METHOD FOR MAKING IT

[75] Inventor: David W. Holdridge, Fullerton, Calif.

[73] Assignee: Swedlow, Inc., Garden Grove, Calif.

[21] Appl. No.: 646,930

[22] Filed: Sep. 4, 1984

[51] Int. Cl.[4] .......................... G02B 5/00; G02C 7/02

[52] U.S. Cl. .................................... 350/319; 350/417; 351/159

[58] Field of Search ....................... 350/319, 411, 417; 351/159, 169

[56] References Cited

U.S. PATENT DOCUMENTS

| | | | |
|---|---|---|---|
| 1,536,828 | 5/1925 | Drescher . | |
| 2,384,540 | 9/1945 | Flint | 350/319 |
| 2,871,756 | 2/1959 | Graves et al. . | |
| 3,012,384 | 12/1961 | Brown et al. . | |
| 3,873,191 | 3/1975 | Veret et al. | 350/417 |
| 3,917,766 | 11/1975 | Howden | 350/417 |
| 4,249,823 | 2/1981 | Task . | |
| 4,310,242 | 1/1982 | Genco et al. . | |
| 4,377,341 | 3/1983 | Task et al. . | |

OTHER PUBLICATIONS

Angular Deviation and Its Effect on Hud-Equipped Aircraft Weapons Sighting Accuracy, by Louis V. Genco, Lt Col, USAF, Air Force Aerospace Medical Research Laboratory, Aug. 1982 (Wright-Patterson Air Force Base, Ohio 45433).

Pilot Reactions to Optical Defects Found in F-111 Bird Impact Resistant Windscreens, by Shelton MacLeod, PhD, Robert G. Eggelston, Major, USAF, Air Force Aerospace Medical Research Laboratory, Dec. 1980 (Wright-Patterson Air Force Base, Ohio 45433).

Computer Analysis and Correction of the Optical Distortion in the F-111 Bird Impact Resistant Windscreen, by Rich Seid, Major, USAF, Air Force Aerospace Medical Research Laboratory, Dec, 1982 (Wright-Patterson Air Force Base, Ohio 45433).

Optical Factors in Aircraft Windshield Design as Related to Pilot Visual Performance, by Walter F. Grether, Jul. 1973, Aerospace Medical Research Laboratory (Wright-Patterson Air Force Base, Ohio).

*Primary Examiner*—John K. Corbin
*Assistant Examiner*—Loha Ben
*Attorney, Agent, or Firm*—Pretty, Schroeder, Breuggemann & Clark

[57] ABSTRACT

A contoured transparency such as an aircraft windshield or canopy, and a method for making it, that provides reduced optical distortion for a pilot seating beneath it. The transparency is configured to have a tailored thickness gradient across its surface such that light passing obliquely through it and converging at a predetermined low distortion point is refracted in such a way the optical distortion is minimized. In one embodiment, the thickness gradient is selected such that light passing obliquely through it and converging on a single point follows a path after exiting the transparency that substantially parallels its path before entering the transparency. This eliminates angular deviation of a line of sight from that specific low distortion point. In another embodiment, the thickness gradient is selected such that the angle between the lines of sight of the pilot's two eyes to a remote target remains unchanged after passing through the transparency. This eliminates binocular deviation.

22 Claims, 8 Drawing Figures

CONTOURED TRANSPARENCY PROVIDING REDUCED OPTICAL DISTORTION AND METHOD FOR MAKING IT

BACKGROUND OF THE INVENTION

This invention relates generally to contoured transparencies such as aircraft windshields and canopies, and, more particularly, to transparencies configured to reduce optical distortion.

Windshields and canopies of modern aircraft are frequently highly contoured, having large amounts of curvature, and the pilots must look through the transparencies at highly oblique angles. These transparency configurations can bring about significant optical distortion and sighting errors. For example, angular deviation of the pilots line of sight can cause objects to be observed in the sky at apparent locations displaced significantly from their actual locations. This is an extremely critical drawback, especially when the objects being sighted are other aircraft.

In addition, the transparency configurations can alter the lines of sight of the pilot's two eyes by different amounts, such that each eye perceives the object to be in a different location. This phenonemon, called binocular deviation, can cause severe eye fatigue and headaches, and in extreme cases can cause image separation, or double vision.

In the past, it has been commonly believed that optical distortion and sighting errors could be minimized by forming the transparencies with precisely uniform thickness over their entire areas. Thus, great care has been taken in manufacturing the tooling and in refining the grinding and polishing techniques used in producing these transparent sheets. Despite this care, transparencies having a uniform thickness still provide significant distortion and sighting errors.

The designers of some aircraft systems, such as Heads-Up Display (HUD) systems, have sought to compensate for some sighting errors introduced by such transparencies by providing corrections based on optical deviation test results. This is believed to unduly complicate the HUD system and thereby to add significantly to its cost.

It should be appreciated from the foregoing that there is a definite need for an improved contoured transparency that provides reduced distortion of light passing through it at an oblique angle. In particular, there is a need for a transparency such as an aircraft windshield or canopy that substantially eliminates optical distortion such as angular deviation, or, alternatively, binocular deviation. The present invention fulfills this need.

SUMMARY OF THE INVENTION

The present invention is embodied in a contoured transparency such as an aircraft windshield or canopy, and a related method for manufacturing it, that minimizes optical distortion for a person, e.g., a pilot, looking through it from a particular low distortion location. The transparency is comprised of a sheet of transparent material that is formed to a selected contour having a concave side and a convex side, with the low distortion location being located in the space adjacent the transparency's concave side. In accordance with the invention, the transparency's thickness varies across its surface in a prescribed fashion, such that light passing obliquely through it and impinging on the low distortion location is substantially undistorted.

In one embodiment, the thickness of the sheet varies in such a way that light passing obliquely through it and impinging on the low distortion location, in this case a single point, follows a path after exiting the transparency that is substantially parallel with the path it follows before entering the transparency. In this fashion, objects such as other aircraft located on the far side of the transparency appear to the pilot, observing with one eye positioned at the low distortion location, to be exactly where they in fact are.

In another embodiment, the low distortion location corresponds to the general location of the pilot's head, and the lines of sight of his two eyes pass obliquely through the transparency to a remote object. In this embodiment, binocular deviation is eliminated by causing the sheet's thickness to vary in such a way that the vertical and horizontal angles between the two lines of sight remain unchanged after passing through the sheet.

In the method of the invention, the transparency is produced by initially providing a sheet of transparent material having a substantially uniform thickness, and by then modifying the sheet to have the prescribed non-uniform thickness across its surface and forming the sheet into the selected contour. The step of modifying can include steps of mounting the sheet on a grinding chuck having a contour complementary to the prescribed non-uniform thickness for the sheet, and by then grinding flat the exposed side of the mounted sheet. The modified sheet will then automatically have the desired thickness gradient. Alternatively, the step of modifying can be performed after the step of forming, using a suitably programmed robot.

Other aspects and advantages of the present invention will become apparent from the following description of the preferred embodiments, taken in conjunction with the accompanying drawings, which illustrate, by way of example, the principles of the invention.

DESCRIPTION OF THE PREFERRED EMBODIMENT

As shown in the accompanying drawings, the invention is embodied in a contoured transparency such as an airplane windshield or canopy that provides reduced optical distortion for a pilot looking through it. Most such airplane canopies are shaped like segments of a right-circular cylinder or cone, with their longitudinal axes generally parallel with the airplane's longitudinal axis. The pilot is seated beneath the concave side of the canopy, with his head typically positioned at a predetermined location between the canopy's longitudinal axis and the canopy itself.

Figure 1:
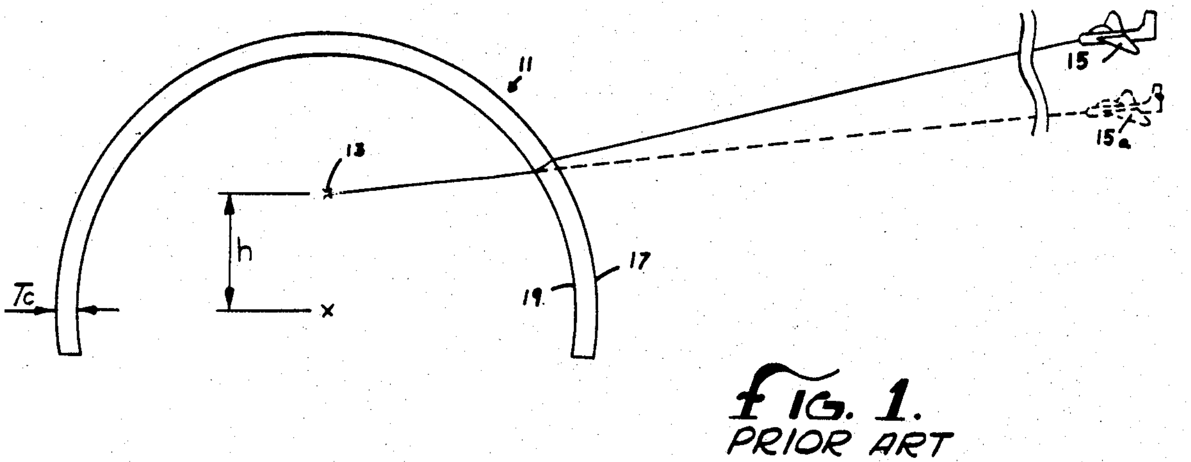
FIG. 1 is a transverse cross-sectional view of a prior art airplane canopy having a uniform thickness, with the optical sighting error it creates being shown schematically in exaggerated form.

FIG. 1 is a transverse cross-sectional view of a prior art airplane canopy 11 formed of a transparent sheet having a substantially uniform thickness $T_c$. The cross-section depicted is substantially circular, and is derived from either a cylindrical or conical canopy configuration. To simplify a description and understanding of the effect the canopy has on the pilot's line of sight, it will be assumed that the pilot has just one eye positioned at a predetermined location designated by the numeral 13.

It will be observed in FIG. 1 that the pilot receives a distorted view of objects (e.g., an airplane 15) located beyond the canopy's convex side. Because of the optical distortion, the airplane is perceived by the pilot to be at a location 15*a* that is spaced from its actual location 15. This optical distortion is depicted in exaggerated form in FIG. 1, and is in fact usually on the order of merely one degree or less. Even this amount of distortion can be extremely dangerous, however. As will be apparent from the following description, this distorted view is caused by light entering and exiting the canopy 11 through portions of the canopy's respective outer and inner surfaces 17 and 19 that are non-parallel.

Figure 2:
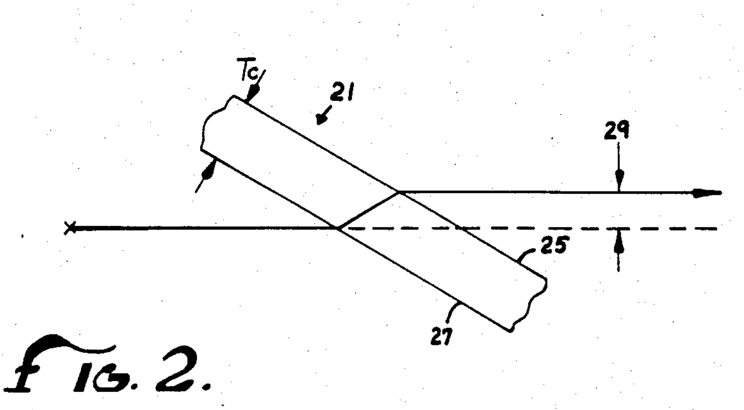
FIG. 2 is a schematic diagram showing the lack of angular deviation of a person's line of sight through a flat transparent sheet of uniform thickness.
Figure 3:
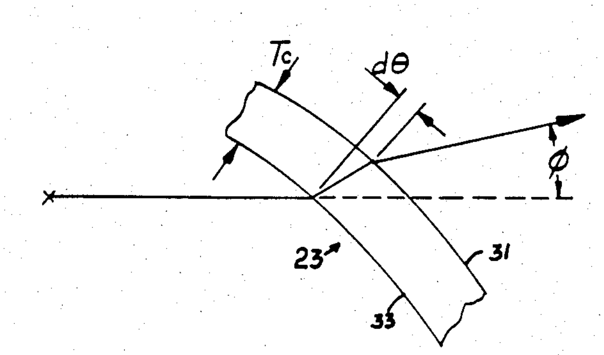
FIG. 3 is a schematic diagram showing the angular deviation of a person's line of sight through a curved transparent sheet of uniform thickness.

The effect a transparent sheet of substantially uniform thickness has on a line of sight passing obliquely through it is depicted schematically in FIGS. 2 and 3. The transparent sheet 21 of FIG. 2 is flat, whereas the transparent sheet 23 of FIG. 3 is uniformly curved. In each case, the pilot's line of sight to a remote object (not shown) is refracted at both surfaces of the transparency, by reason of the difference between the refractive indices of the sheet itself and the air surrounding the sheet. The amount of refraction also depends, of course, on the initial angle of incidence and it can be determined by the well-known Snell's law.

When the slopes of the sheet's respective outer and inner surfaces 25 and 27 are parallel, as in the example of FIG. 2, the amount of refraction occuring at the two surfaces is identical and the light follows a path after exiting the sheet that is parallel with its path before entering the sheet. As depicted in FIG. 2, the refraction causes only a slight lateral deviation of the line of sight, designated by the numeral 29, which is ordinarily of little or no consequence.

In the case of the uniformly curved transparency 23 of FIG. 3, on the other hand, the amount of refraction is different at the sheet's respective outer and inner surfaces 31 and 33. This difference results because the beam passes through points on the respective surfaces that are circumferentially spaced from each other, and thus not parallel with each other. The resulting angular deviation, which is designated by the angle $\phi$, can be as much as one degree of curvature, depending upon the angle at which the beam initially impinges on the sheet.

Figure 4:
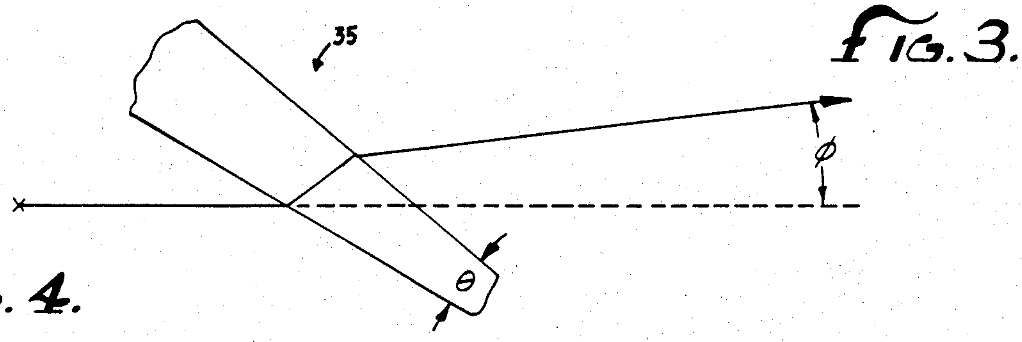
FIG. 4 is a schematic diagram showing the angular deviation of a person's line of sight through a transparent wedge.

The effect of the angular deviation provided by the uniformly curved transparent sheet 23 of FIG. 3 is analogous to the deviation provided by a transparent wedge 35, depicted schematically in FIG. 4. The amount of angular deviation provided by the two transparencies is identical when the angle $\theta$ of the wedge (FIG. 4) is equal to the angular spacing $d\theta$ between the incident and exit points in the curved sheet.

The angular deviation of a line of sight produced by the contoured transparency 11 of FIG. 1 can be extremely dangerous, especially when the object whose exact position is in the sky is being distorted is another aircraft 15. There is therefore a significant need for a transparency configuration that substantially eliminates this angular deviation.

Figure 5:
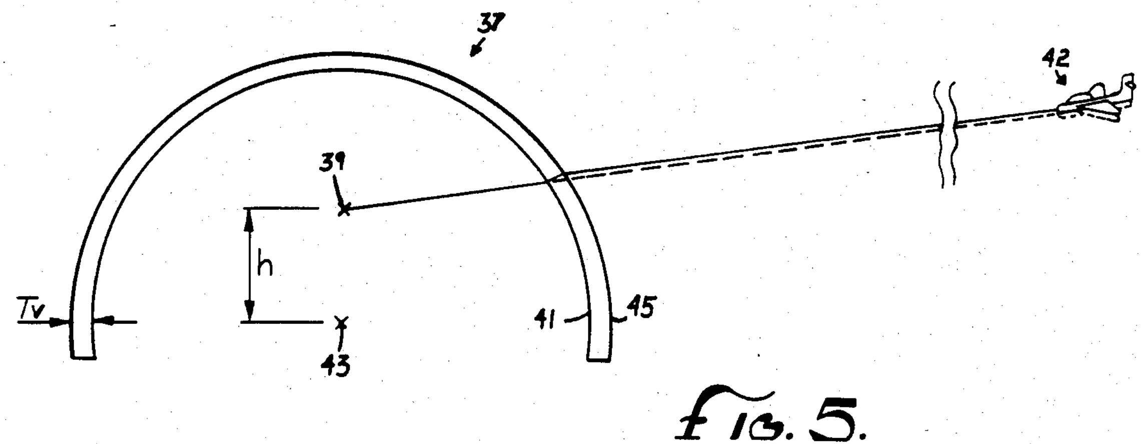
FIG. 5 is a transverse cross-sectional view of one embodiment of the present invention, with the lack of angular deviation of the line of sight from a predetermined low distortion point being shown schematically.

In a first embodiment of the invention, depicted in FIG. 5, a contoured transparency 37 is configured to have a prescribed non-uniform thickness $T_v$ such that light passing obliquely through it and converging on a particular point 39 spaced from its concave side 41 follows a path after exiting the transparency that is substantially parallel with its path before entering the transparency. Angular deviation is thereby eliminated, and a remote object such as an airplane 42 appears to the pilot having one eye at the point 39 to be precisely where it actually is.

The contoured transparency of FIG. 5 has an outer surface with a shape that is substantially the same as that of a section of a cylinder or cone, which is typical of aircraft transparencies. In the example of FIG. 5, the particular position 39 at which angular deviation is minimized is located above the transparency's central axis 43, between the axis and the transparency itself. To achieve minimum angular deviation for that position, the transparency has a thickness that increases generally geometrically as a function of distance from the transparency's centerline. This is shown in exaggerated form in FIG. 5. The procedure for determining this thickness gradient is described in detail below.

Figure 6:
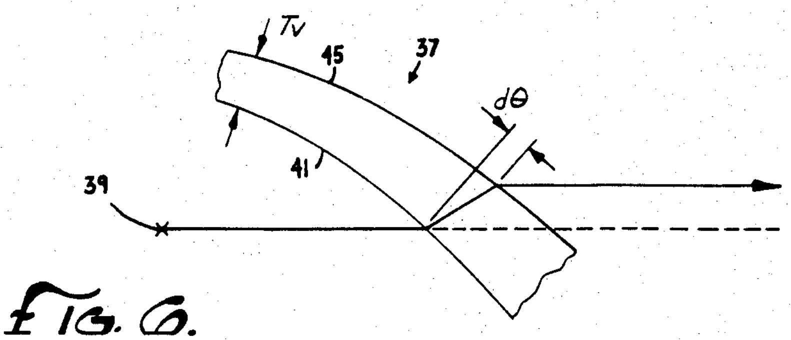
FIG. 6 is an enlarged diagram of a segment of the contoured transparency of FIG. 5, showing, in schematic form, the lack of angular deviation of the line of sight.

FIG. 6 depicts a small section of the transparency 37 of FIG. 5, and shown in schematic form how a beam of light is refracted at the transparency's outer and inner surfaces 45 and 41, respectively, such that its paths before and after passing through the transparency are substantially parallel. Light passing through the transparency from a remote location (not shown) to the low distortion position 39 first impinges on the transparency's outer surface 45, whereupon it is refracted in accordance with the well-known Snell's law. When the light reaches the transparency's inner surface 41, it is refracted again. In accordance with the invention, the transparency's inner and outer surfaces are configured such that the slopes of the particular segment through which the beam passes are parallel to each other. In this fashion, the light beam is refracted by the same amount at the two surfaces and the beam therefore experiences substantially no angular deviation.

It will be appreciated that the outer surface 45 of the transparency 37 of the invention need not have a cylindrical or conical configuration, but rather can have any contoured shape. The special case of a cylindrical configuration is used for purposes of this description so that the principles of the invention can be understood with greater clarity. For any contour, whether it is symmetrical or asymmetrical, the thickness of each point on the transparency is selectively controlled such that light passing obliquely through it and converging on a single low distortion position follows a path after exiting the transparency that is substantially parallel with the path the light followed before entering the transparency.

Attached as Appendix 1 to this application is the listing of a computer program suitable for use with a TRS 80 desk top computer, for calculating the optimum thickness gradient for a cylindrically-shaped transparency having an inside radius of fifteen units and a thickness at its centerline of one unit. The transparency's centerline is defined as the locus of points lying closest to the low distortion position 39, for all parallel sections along the transparency's longitudinal axis, which includes the point lying immediately above the geometric axis 43 in FIG. 5. The various locations on the transparency whose desired thicknesses are specified by the program are designated by the coordinates "x" and "s", with "x" indicating its location along the transparency's longitudinal axis and with "s" indicating its spacing from the centerline.

The first portion of the program determines whether or not the line of sight is through the transparency or beyond its peripheral edge. The second portion defines the angle between the pilot's line of sight and a normal to the transparency at the point on the transparency's inner surface intersected by the line of sight. The third portion of the program traces the ray through the transparency, to determine the required optical prescription. In particular, it determines the amount of refraction produced at the transparency's inner surface and calculates the thickness required to produce an equivalent slope and thus equivalent refraction at the transparency's outer surface. The program also determines the angular deviation that would be created by a transparency having a constant thickness. Ray tracing begins with the coordinates "x" and "s" both being zero and proceeds until "s" is beyond the transparency's peripheral edge. The coordinate "x" is then moved forward by five units and the process repeated, with the coordinate "s" initially at zero.

The results of running the computer program are included with the program listing. These results indicate that the transparency's thickness increases in a generally exponential fashion from the centerline to the peripheral edge. This exponential increase also varies slightly from the front to the back of the transparency, since the angle at which the line of sight first impinges on the transparency's inside surface varies from front to back. A transparency having the specified thickness gradient exhibits no angular deviation for light passing through it and impinging on a predetermined low distoriton point. The deviations listed, which are on the order of $10^{-7}$ radians, are caused by round-off errors within the computer.

In this example, the pilot's eye is located between the transparency's longitudinal axis and the transparency itself, resulting in increased thickness at the transparency's edges. If the pilot's eye position were located on the other side of the transparency's axis, however, the transparency would have an increased thickness near its centerline and be thinner towards its edges.

Figure 7:
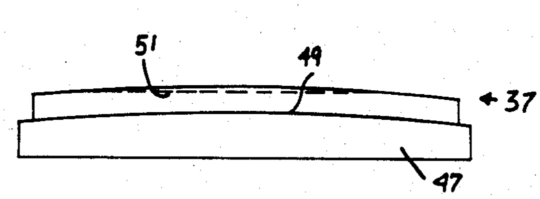
FIG. 7 is a side elevational view of apparatus for use in producing the contoured transparency of FIG. 5.

With reference now to FIG. 7, there is shown, in simplified form, one suitable apparatus for use in producing a transparent sheet having the thickness gradient desired for the contoured transparency 37 of the invention. The apparatus includes a table or grinding chuck 47 having a precisely-machined contour on its upper surface 49 that complements the desired thickness gradient. A transparent sheet of uniform thickness is placed onto the chuck and pulled into intimate contact with it using a conventional vacuum system. The exposed surface of the sheet is then ground flat and polished, as indicated by the broken line 51, to produce a sheet having the desired thickness gradient. After removal from the chuck, the sheet is formed into the desired contour. The sheet can be formed from any of a number of conventional transparent materials, such as acrylic or polycarbonate, and can alternatively be a laminated composite of those and other materials.

In an alternative technique, not shown in the drawings, the transparent sheet is first formed into the desired contour and then ground to the prescribed thickness gradient. The grinding can be accomplished by vacuuming the formed sheet onto a male plug having a contour desired for the transparency's inner surface and then grinding the outer surface to its prescribed contour, using, for example, a suitably programmed robot.

The first embodiment of the invention described above eliminates angular deviation of light passing obliquely through the transparency and impinging on the single, predetermined point. This is an extremely important benefit in many applications, especially when the pilot is sighting a target using just one eye, located at the predetermined point.

Eliminating angular deviation for one eye, however, does not necessarily minimize other optical distortion phenomena, such as binocular deviation. Binocular deviation is caused when a person's two eyes perceive an object as being located in different directions, and can result in eye fatigue, headaches, and, in extreme cases, double vision. There is therefore sometimes a need for a contoured transparency that minimizes such binocular deviation.

Figure 8:
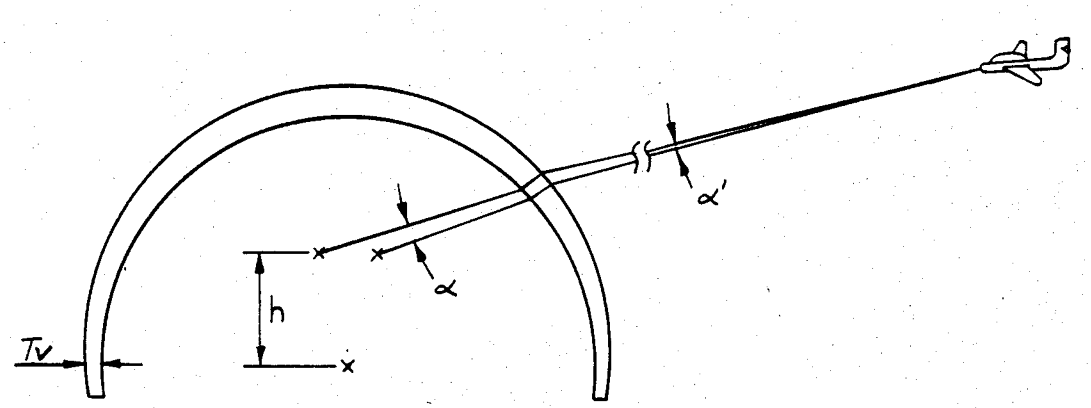
FIG. 8 is a transverse cross-sectional view of a second embodiment of the present invention, with the lack of binocular deviation of the line of sight of a pilot seated at a predetermined low distortion location being shown schematically.

In a second embodiment of the invention, depicted in FIG. 8, a contoured transparency 53 is configured to have a non-uniform thickness $T_v$ such that the horizontal and vertical angles between the lines of sight from a pilot's two eyes 55 and 57 to a remote object such as an airplane 59 is the same before and after passing through the transparency. The two images are therefore superimposed on each other, and eye fatigue and related visual problems are eliminated.

The selection of an optimum thickness gradient for the transparency 53 of this embodiment of the invention is preferably performed using an iterative technique. A selected gradient defined by a specified geometric formula is first analyzed to determine the binocular deviation it provides. This formula is then adjusted and the resulting effect on binocular deviation is determined. The process is repeated until binocular deviation is reduced to an acceptable level.

Attached as Appendix II to this application is the listing of a second computer program suitable for use with a TRS 80 desk top computer, for determining the binocular deviation for a transparency having an outside surface defined as a right-circular cone and an inside surface defined as an elliptical cone. Four variables of the elliptical cone can be selectively adjusted, including the lengths of its major and minor axes, and the displacement and angle of its axis relative to the axis of the right circular cone. By iteratively optimizing the four variables in sequence, an optimal thickness gradient for the transparency can be readily determined.

In the case where the pilot is seated with his eyes located at the positions 55 and 57, between the transparency's longitudinal axis and the transparency 53 itself, the transparency that provides minimal binocular deviation is slightly thicker at its middle than at its lateral periphery. This is generally opposite from the thickness gradient of the transparency 37 of FIG. 5.

The transparency 53 of FIG. 8 can be produced using either of the techniques described above with respect to the transparency 37 of FIG. 5.

It should be appreciated from the foregoing description that the present invention provides an improved contoured transparency having a tailored thickness gradient that substantially eliminates optical distortion of one kind or another. In one embodiment, the transparency's thickness gradient is selected such that all light passing obliquely through it and converging on a single low distortion point follows a path after exiting the transparency that is substantially parallel with its path before entering the transparency. In another embodiment, the transparency's thickness gradient is selected such that the horizontal and vertical angles between the lines of sight of the pilot's two eyes to a remote object remain unchanged after passing through the transparency. This eliminates binocular deviation.

Although the invention has been described in detail with reference to the presently preferred embodiments, it will be understood by those of ordinary skill in the art that various modifications can be made without departing from the invention. Accordingly, the invention is limited only by the following claims.

This set of equations was entered in a TRS 80 desktop computer. The program is shown below.

```
10 TO=1.0
20 DX=5.0
30 N=1.49
40 T=TO
50 X=0.0
60 DS=1.0
70 R=15.
80 Y1=3.
90 Q=30*3.1416/180
100 V1=2.
110 LPRINT" X        S        DT        T        PHI          PHI"
120 LPRINT"                                      CORRECTED    UNCORRECTED"
130 LPRINT
140 S=DS
150 T1=S/R
160 W=0.
170 H=R*COS(T1)-Y1
180 U=H*COS(Q)-X*SIN(Q)
190 V=H*SIN(Q)+X*COS(Q)
200 A=Y1/COS(Q)+V1*TAN(Q)
210 IF U<-A THEN 630
220 IF V<V1 THEN 630
230 Z=R*SIN(T1)
240 TH=ATN(Z/H)
250 ALFA=TH-T1
260 R1=SQR (H[2+(R*SIN(T1))[2)
270 EPS=ATN(X/R1)
280 B=(TAN(ALFA))[2+(TAN(EPS))[2
290 T1=ATN(SQR (B))
300 B=SIN(T1)/N
310 T2=ATN(B/SQR (1-B[2))
320 P1=ATN(TAN(EPS)/TAN(ALFA))
330 A2=ATN(TAN(T2)*COS(P1))
340 E2=ATN(TAN(T2)*SIN(P1))
350 S1=T*TAN(A2)
360 R2=R+T
370 DT=S1/R2
380 D3=DT
390 A3=A2-S1/R2+D3
400 E3=E2
410 B=(TAN(A3))[2+(TAN(E3))[2
420 T3=ATN(SQR(B))
430 B=N*SIN(T3)
440 T4=ATN(B/SQR(1-B[2))
450 P2=ATN(TAN(E3)/TAN(A3))
460 A4=ATN(TAN(T4)*COS(P2))
470 E4=ATN(TAN(T4)*SIN(P2))
480 DA=A4-ALFA-D3+S1/R2
490 DE=E4-EPS
500 B=(TAN(DA))[2+(TAN(DE))[2
510 IF W=0 THEN 520 ELSE 580
520 PHI=ATN(SQR(B))
530 R2=R+TO
540 D3=0.0
550 S1=TO*TAN(A2)
560 W=1
570 GOTO 390
580 P3=ATN(SQR(B))
590 LPRINT X,S.DT.T.PHI,P3
600 T=T+(DS*(R+T)/R)*TAN(DT)
610 S=S+DS
620 GOTO 150
630 X=X+DX
640 LPRINT
650 T=TO
```

```
660 IF S=DS THEN 680
670 GOTO 140
680 END
```

APPENDIX I

The results of this analysis are tabulated below for each section cut (x) through the cylinder.

| x | S | CT | T | PHI CORRECTED | PHI UNCORRECTED |
|---|---|---|---|---|---|
| 0 | 1 | 4.98143E-04 | 1 | 0 | 3.433E-04 |
| 0 | 2 | 1.39133E-03 | 1.00074 | 0 | 6.81976E-04 |
| 0 | 3 | 2.07356E-03 | 1.00223 | 0 | 1.01316E-03 |
| 0 | 4 | 2.74778E-03 | 1.00444 | 0 | 1.34333E-03 |
| 0 | 5 | 3.40188E-03 | 1.00738 | 0 | 1.66394E-03 |
| 0 | 6 | 4.03387E-03 | 1.01101 | 0 | 1.9734E-03 |
| 0 | 7 | 4.64381E-03 | 1.01531 | 0 | 2.26339E-03 |
| 0 | 8 | 5.22872E-03 | 1.02027 | 0 | 2.54403E-03 |
| 0 | 9 | 5.78173E-03 | 1.02586 | 0 | 2.80391E-03 |
| 0 | 10 | 6.30243E-03 | 1.03204 | 0 | 3.04896E-03 |
| 0 | 11 | 6.78834E-03 | 1.03077 | 0 | 3.27337E-03 |
| 0 | 12 | 7.23834E-03 | 1.04603 | 0 | 3.4747E-03 |
| 0 | 13 | 7.64994E-03 | 1.05377 | 0 | 3.65483E-03 |
| 0 | 14 | 8.02233E-03 | 1.06196 | 0 | 3.81348E-03 |
| 0 | 15 | 8.35443E-03 | 1.07055 | 0 | 3.94731E-03 |
| 0 | 16 | 8.64577E-03 | 1.0795 | 0 | 4.05928E-03 |
| 5 | 1 | 6.67093E-04 | 1 | 0 | 3.73399E-04 |
| 5 | 2 | 1.33996E-03 | 1.00071 | 0 | 7.43319E-04 |
| 5 | 3 | 1.9843E-03 | 1.00213 | 3.74507E-07 | 1.10817E-03 |
| 5 | 4 | 2.62736E-03 | 1.00425 | 0 | 1.46443E-03 |
| 5 | 5 | 3.23453E-03 | 1.00705 | 0 | 1.80973E-03 |
| 5 | 6 | 3.86305E-03 | 1.01052 | 0 | 2.14183E-03 |
| 5 | 7 | 4.44949E-03 | 1.01465 | 0 | 2.45733E-03 |
| 5 | 8 | 5.01091E-03 | 1.0194 | 0 | 2.75331E-03 |
| 5 | 9 | 5.54462E-03 | 1.02475 | 0 | 3.02403E-03 |
| 5 | 10 | 6.04814E-03 | 1.03067 | 3.74507E-07 | 3.29133E-03 |
| 5 | 11 | 6.51933E-03 | 1.03714 | 3.74507E-07 | 3.53431E-03 |
| 5 | 12 | 6.95634E-03 | 1.04411 | 0 | 3.77745E-03 |
| 5 | 13 | 7.35735E-03 | 1.05155 | 0 | 3.93465E-03 |
| 5 | 14 | 7.72095E-03 | 1.05942 | 0 | 4.08659E-03 |
| 5 | 15 | 8.04633E-03 | 1.06769 | 0 | 4.23395E-03 |
| 5 | 16 | 8.33315E-03 | 1.07631 | 0 | 4.33633E-03 |
| 5 | 17 | 8.57808E-03 | 1.08524 | 0 | 4.43365E-03 |
| 5 | 18 | 8.7933E-03 | 1.09443 | 0 | 4.48673E-03 |
| 5 | 19 | 8.94813E-03 | 1.10386 | 0 | 4.53586E-03 |
| 5 | 20 | 9.07193E-03 | 1.11347 | 0 | 4.54263E-03 |
| 5 | 21 | 9.15491E-03 | 1.12321 | 3.74507E-07 | 4.5364E-03 |
| 5 | 22 | 9.19738E-03 | 1.13305 | 0 | 4.50994E-03 |
| 5 | 23 | 9.19947E-03 | 1.14294 | 0 | 4.46319E-03 |
| 10 | 1 | 5.94068E-04 | 1. | 0 | 4.46435E-04 |
| 10 | 2 | 1.16473E-03 | 1.00063 | 0 | 8.88513E-04 |
| 10 | 3 | 1.76591E-03 | 1.0019 | 0 | 1.33399E-03 |
| 10 | 4 | 2.34364E-03 | 1.00378 | 0 | 1.74511E-03 |
| 10 | 5 | 2.90598E-03 | 1.00629 | 0 | 2.15369E-03 |
| 10 | 6 | 3.4531E-03 | 1.00939 | 0 | 2.54139E-03 |
| 10 | 7 | 3.98335E-03 | 1.01307 | 0 | 2.90903E-03 |
| 10 | 8 | 4.49083E-03 | 1.01732 | 0 | 3.2533E-03 |
| 10 | 9 | 4.97679E-03 | 1.02212 | 0 | 3.57178E-03 |
| 10 | 10 | 5.43663E-03 | 1.02743 | 0 | 3.86394E-03 |
| 10 | 11 | 5.86944E-03 | 1.03324 | 0 | 4.12598E-03 |
| 10 | 12 | 6.27359E-03 | 1.03952 | 0 | 4.35933E-03 |
| 10 | 13 | 6.64536E-03 | 1.04632 | 0 | 4.5633E-03 |
| 10 | 14 | 6.98504E-03 | 1.05333 | 0 | 4.73317E-03 |
| 10 | 15 | 7.29095E-03 | 1.06081 | 0 | 4.88148E-03 |
| 10 | 16 | 7.56183E-03 | 1.06862 | 9.36369E-08 | 4.9965E-03 |
| 10 | 17 | 7.79687E-03 | 1.07672 | 0 | 5.083E-03 |
| 10 | 18 | 7.99534E-03 | 1.08507 | 0 | 5.14116E-03 |
| 10 | 19 | 8.15673E-03 | 1.09365 | 0 | 5.17334E-03 |
| 10 | 20 | 8.28074E-03 | 1.1024 | 0 | 5.17853E-03 |
| 15 | 1 | 5.13367E-04 | 1 | 3.86033E-07 | 5.28074E-04 |
| 15 | 2 | 1.02193E-03 | 1.00055 | 0 | 1.0514E-03 |
| 15 | 3 | 1.52667E-03 | 1.00164 | 3.74507E-07 | 1.5637E-03 |
| 15 | 4 | 2.02416E-03 | 1.00327 | 0 | 2.06133E-03 |
| 15 | 5 | 2.51313E-03 | 1.00542 | 2.8088E-07 | 2.53914E-03 |
| 15 | 6 | 2.98833E-03 | 1.00811 | 3.74507E-07 | 2.99417E-03 |
| 15 | 7 | 3.45039E-03 | 1.01129 | 3.74507E-07 | 3.43195E-03 |
| 15 | 8 | 3.89606E-03 | 1.01498 | 8.37424E-07 | 3.82056E-03 |
| 15 | 9 | 4.33747E-03 | 1.01914 | 0 | 4.18657E-03 |
| 15 | 10 | 4.73043E-03 | 1.02375 | 1.87334E-07 | 4.51966E-03 |
| 15 | 11 | 5.11501E-03 | 1.02881 | 3.74507E-07 | 4.81748E-03 |
| 15 | 12 | 5.4754E-03 | 1.03427 | 8.37424E-07 | 5.08053E-03 |
| 15 | 13 | 5.80993E-03 | 1.04013 | 0 | 5.30695E-03 |
| 15 | 14 | 6.11703E-03 | 1.04634 | 3.74507E-07 | 5.49884E-03 |
| 15 | 15 | 6.39538E-03 | 1.05288 | 0 | 5.65493E-03 |
| 15 | 16 | 6.64374E-03 | 1.05973 | 0 | 5.7773E-03 |
| 15 | 17 | 6.86113E-03 | 1.06684 | 0 | 5.86634E-03 |
| 20 | 1 | 4.39415E-04 | 1 | 3.86033E-07 | 6.01098E-04 |
| 20 | 2 | 8.76834E-04 | 1.00047 | 7.49013E-07 | 1.19638E-03 |
| 20 | 3 | 1.31043E-03 | 1.0014 | 5.39633E-07 | 1.77853E-03 |
| 20 | 4 | 1.73837E-03 | 1.0028 | 5.39633E-07 | 2.34413E-03 |
| 20 | 5 | 2.15884E-03 | 1.00466 | 5.99504E-07 | 2.88679E-03 |
| 20 | 6 | 2.57E-03 | 1.00696 | 3.74507E-07 | 3.40348E-03 |
| 20 | 7 | 2.97001E-03 | 1.0097 | 5.04196E-07 | 3.88588E-03 |
| 20 | 8 | 3.35701E-03 | 1.01287 | 9.36369E-08 | 4.33633E-03 |
| 20 | 9 | 3.7293E-03 | 1.01646 | 4.68134E-07 | 4.74963E-03 |
| 20 | 10 | 4.08483E-03 | 1.02044 | 8.37424E-07 | 5.12436E-03 |
| 20 | 11 | 4.42314E-03 | 1.0248 | 2.8088E-07 | 5.45738E-03 |
| 20 | 12 | 4.7795E-03 | 1.02953 | 1.87334E-07 | 5.7513E-03 |
| 20 | 13 | 5.03336E-03 | 1.03459 | 0 | 6.00398E-03 |
| 25 | 1 | 3.79649E-04 | 1 | 0 | 6.61014E-04 |
| 25 | 2 | 7.57695E-04 | 1.00041 | 0 | 1.3146E-03 |
| 25 | 3 | 1.13367E-03 | 1.00121 | 4.68134E-07 | 1.95534E-03 |
| 25 | 4 | 1.50309E-03 | 1.00242 | 3.74507E-07 | 2.57738E-03 |
| 25 | 5 | 1.86748E-03 | 1.00403 | 7.73067E-07 | 3.17738E-03 |
| 25 | 6 | 2.22438E-03 | 1.00602 | 0 | 3.74065E-03 |
| 25 | 7 | 2.57199E-03 | 1.00839 | 9.36369E-08 | 4.27373E-03 |
| 25 | 8 | 2.90901E-03 | 1.01114 | 5.6176E-07 | 4.76738E-03 |
| 25 | 9 | 3.23782E-03 | 1.01424 | 3.74507E-07 | 5.22238E-03 |

APPENDIX II

```
10 '            PROGRAM NAME: BINOC/BAS
20 '            BY R. HOPKINS & D. HOLDRIDGE
30 '            LATEST REVISION DATE: 15 FEB 1984
40 '
50 '
60 '            **INPUT DATA**
70 POKE&H4210,249     'SPEED UP ROUTINE FOR TRS 80 MODEL IV
80 A(2)=15.748-    'A,B & C CONSTANTS FOR ELLIPTIC CONE ON OML
90 B(2)=15.748
100 C(2)=261.99
110 T=1.0236           'THICKNESS OF W/S AT CENTERLINE
115 DV=0
120 'FOR DV=0.29 TO .33 STEP .02    'VERTICAL OFFSET FOR IML CONE AXIS TO VARY B(1) TERM
130 'FOR PT=0 TO .1 STEP .1
140 DV(1)=DV
150 'DV(1)=.2450              'V OFFSET
160 C5=0                'COUNTER
170 FL=0:FZ=0
180 PT=0                     'PRESCRIPTION TERM TO VARY A(1) VALUE
190 BE=ATN(B(2)/C(2))    'BETA ANGLE, BETWEEN Z AXIS & W AXIS
200 DW(1)=T/SIN(BE)-DV(1)/TAN(BE)         'W OFFSET
210 TH=27*3.1415927/180-BE          'THETA, 1/2 OF CONE ANGLE
220 A(1)=A(2)+(PT-T)*(SQR((C(2)*C(2))+(A(2)*A(2))))/C(2)       'A,B,& C CONSTANTS FOR IML ELLIPTIC CONE EQN
230 B(1)=B(2)-T/COS(BE)+DV(1)
240 XE=0                    'EYE POSITION XE,YE,ZE
250 ZE=251.4395
260 YE=113.273
270 'YE=ZE*TAN(TH)                'EYE ON CONE CL CONDITION
280 LPRINTCHR$(15)
290 LPRINT"XE,YE,ZE: ";XE;YE;ZE;
300 LPRINT"   PRESCRIPTION VARIATION: ";PT;
305 LPRINT"                  LAST PROGRAM UPDATE: 15 FEB '84
310 LPRINT"VALUES OF OFFSETS: DV(1)=";DV(1);",  DW(1)=";DW(1);",  CL THICKNESS T=";T
320 AN=0                'AZIMUTH COUNTERS AN,AM,DA
330 AM=55
340 DA=5
350 EN=-20                      'ELEVATION COUNTERS EN,EM,DE
360 EM=15
370 DE=5
380 TQ=120  'TQ=ABS(AM-AN)/ABS(DA)*ABS(EN-EM)/ABS(DE)      'SIZE OF DIM STATEMENT FOR VC GENERATION
390 DIM Y(6,TQ)
400 ZF=0        'Z AXIS LIMITS FORWARD AND REAR, ZF & ZR
410 ZR=ZE
420 'YL=95         'Y AXIS LIMITS LOW & HIGH, YL & YH
430 'YH=125
440 C(1)=C(2)-DW(1)
450 CLS
460 PRINT"DIFFERENCES BETWEEN SLOPE:";A(1)/C(1)-A(2)/C(2);B(1)/C(1)-B(2)/C(2)
470 FOR P=1TO 500:NEXT P
480 CT=COS(TH)
490 ST=SIN(TH)
500 TT=TAN(TH)
510 DR=ATN(9999999999)/90     'DEGREE TO RADIAN CONVERSION
520 '                     COMPUTE
530 CLS
540 PRINT@540,"PROGRAM RUNNING, SO WAIT AWHILE!"
550 LPRINTTAB(5)"AZ";TAB(25)"EL";TAB(45)"AZ(1)";TAB(65)"EL(1)";TAB(85)"AZ(B)";TAB(105)"EL(B)"
560 FOR EL=EN TO EM STEP DE
570 FOR AZ=AN TO AM STEP DA
560 FOR EL=EN TO EM STEP DE
570 FOR AZ=AN TO AM STEP DA
580 'FOR EL=EN TO EM STEP DE
590 GOTO 680             'PRINT VALUES OF EQNS EVEN IF NOT ON W/S
600 IF EL=15 AND AZ=30 THEN NEXTAZ
610 IF EL=15 AND AZ=45 THEN LPRINT"-----------"ELSE 630
620 NEXTAZ:NEXTEL:GOTO 2460
630 IF EL=5 AND AZ=45 THEN LPRINT"-----------"ELSE 650
640 NEXTAZ:NEXTEL
650 IF EL=-5 AND AZ=45 THEN LPRINT"-----------"ELSE 670
660 NEXT AZ:NEXT EL
670 'CONT OF PROGRAM
680 UE=XE          'CONVERSION OF EYE POSITION FROM X,Y,Z COORD TO U,V,W COORD
690 VE=(YE-ZE*TT)*CT
700 WE=ZE/CT+VE*TT
710 AC=AZ*DR
720 EC=EL*DR
730 'LPRINT"AZ,AC,EL,EC: ";AZ;AC,EL;EC
740 M=1
750 N=1
760 CLS
770 SG=TH+EC          'VALUE OF SIGMA-- ANGLE BETWEEN W AXIS AND LOS IN V-W PLANE
780 ZT=ATN(TAN(AC)*COS(EC)/SIN(SG))             'VALUE OF ZETA--ANGLE BETWEEN V AXIS AND LOC IN U-V PLANE
790 'LPRINT"SG(";N-1;")/DR =";SG/DR;"     ZT(";N-1;")/DR =";ZT/DR
800 UO=UE
810 VO=VE
820 WO=WE
830 NI=1.49     'INDEX OF REFRACTION, AIR TO ACRYLIC
840 D=TAN(SG)      'CONSTANTS D,E,F,G,H,I,J  FOR SOLVING QUADRATIC EQN
850 E=VO+WO*D
860 F=D*TAN(ZT)
870 G=UO-WO*F
880 H=(F/A(N))[2+(D/B(N))[2-(1/C(N))[2
890 I=2*(G*F/(A(N)[2)-E*D/(B(N)[2)-D*DV(N)/(B(N)[2)+DW(N)/(C(N)[2))
900 J=(G/A(N))[2+(E/B(N))[2+(DV(N)/B(N))[2+2*E*DV(N)/(B(N)[2)-(DW(N)/C(N))[2
910 'LPRINT"D,E,F,G,H,I,J: "D;E;F;G;H;I;J
```

```
920 CLS
930 K=SQR(I[2-4*H*J)          'SOLVING FOR QUADRATIC EQN
940 W=(-I-K)/(2*H)
950 L=1     'FIRST ROOT OF EQN
960 U=G+W*F
970 V=E-W*D
980 Z=W*CT-V*ST
990 Y=W*ST+V*CT
1000 X=U '
1010 PRINT@540,"PROGRAM IS RUNNING, SO WAIT AWHILE!"
1020 'LPRINT "K,W,U,V,Z,Y: ";K;W;U;V;Z;Y
1030 IF N=2 THEN 1160
1040 IF (Z>ZF)AND(Z<ZR)THEN 1280 ELSE 1060     'TEST TO SEE IF POINT IS ON W/S
1050 'IF (Y>YL)AND(Y<YH)THEN 1130 ELSE 890
1060 IFL=2 THEN 1120
1070 L=2    '2ND ROOT OF QUAD EQN
1080 W=(-I+K)/(2*H)
1090 XO=U:YO=Y:ZO=Z
1100 X=U
1110 GOTO 960
1120 'LPRINT "AZ=";AZ;", EL=";EL;",  SIGHT OFF PART--- X,Y,Z INTERSECTIONS NOT ON PART:";XO;YO;ZO,X;Y;Z
1130 'LPRINT
1140 NEXT AZ:LPRINT"-----------":NEXT EL:GOTO 2510
1150 'NEXTEL:NEXTAZ:GOTO 1348
1160 EO=(W-WO)[2+(V-VO)[2+(U-UO)[2   'ER & EO ARE SQUARES OF DISTANCES BETWEEN IML & OML INTERSECTIONS
1170 WB=(-I+K)/(2*H)
1180 VB=E-WB*D
1190 UB=G+WB*F
1200 ER=(WB-WO)[2+(VB-VO)[2+(UB-UO)[2
1210 CLS
1220 IF ER<EO THEN 1280
1230 W=WB
1240 U=UB
1250 V=VB
1260 '
1270 'LPRINT"N,UC,VC,WC: ";N;UC;VC;WC
1280 'LPRINT"X,Y,Z INTERSECTION ON W/S AT ROOT L=";L;": ",X;Y;Z
1290 PRINT@540,"PROGRAM IS RUNNING, SO WAIT AWHILE!"
1300 IF V=0 AND DV(N) =0THEN B1=0 ELSE 1320
1310 B2=999999:GOTO 1330
1320 B2=(B(N)/A(N))[2*U/(V+DV(N))
1330 C2=(C(N)/B(N))[2*(V+DV(N))/(W-DW(N))
1340 IF B2=999999 THEN 1370 ELSE B1=ATN(B2)    'B1 IS THE NORMAL ANGLE IN U-V PLANE
1350 IF C2=0 THEN C1=90*DR ELSE 1370    'C1 IS THE NORMAL ANGLE IN THE V-W PLANE
1360 GOTO 1410
1370 C1=ATN(C2)
1380 '
1390 '
1400 'BEGIN OF RAY TRACE ROUTINE
1410 ED=SQR((V-VO)[2+(WO-W)[2)      'CONVERTING NORMAL TO AN AXIS FOR RAY TRACING
1420 EF=ABS(ED*SIN(90*DR-C1+SG))
1430 BF=SQR((V/C2)[2+V[2)
1440 IF V =0 OR B2=0 THEN AB=90*DR ELSE 1460
1450 GOTO 1470
1460 AB=ABS(ATN(BF/(V*B2)))
1470 IF (U-UO)=0 THEN AE=90*DR ELSE 1490
1480 GOTO 1500
1490 AE=ABS(ATN(EF/(U-UO)))
1500 AI=AB-AE
1510 EG=ABS(ED*COS(90*DR-C1+SG))
1520 EE=SQR(EF[2+(U-UO)[2)
1530 EH=ABS(EE*COS(AI))
1540 IF EH=0 THEN EI=90*DR ELSE 1560
1550 GOTO 1570
1560 EI=ATN(EG/EH)
1570 AP=INT(AI*100/DR)/100
1580 CLS
1590 EP=INT(EI*100/DR)/100
1600 'LPRINT"B1/DR, C1/DR:";B1/DR,C1/DR
1610 'LPRINT"AB/DR,AE/DR,(90*DR-C1+SG)/DR: ";AB/DR;AE/DR;(90*DR-C1+SG)/DR
1620 'LPRINT"ED,EF,BF,EG,EE,EH: ";ED;EF;BF;EG;EE;EH
1630 'LPRINT N;"I",AP,EP
1640 PH=TAN(AI)[2+TAN(EI)[2    'CALCULATING PHI
1650 PH=ATN(SQR(PH))
1660 PH=SIN(PH)/NI
1670 TP=PH/SQR(1-PH[2)
1680 PRINT@540,"PROGRAM IS RUNNING, SO WAIT AWHILE!"
1690 IF ABS(TAN(AI))>0THEN 1720
1700 PS=90*DR
1710 GOTO 1750
1720 PS=ATN(TAN(EI)/TAN(AI))
1730 IF ABS(AI)=AI THEN 1750
1740 TP=-TP
1750 AR=ATN(TP*COS(PS))      'ALPHA ANGLE
1760 EQ=ATN(TP*SIN(PS))       'EPSILON ANGLE
1770 AT=INT(AR*100/DR)/100
1780 ET=INT(EQ*100/DR)/100
1790 'LPRINT"AR,EQ: ";AR,EQ
1800 'LPRINT N;"R",AT,ET
1810 HG=ABS(EH*TAN(EQ))      'CONVERTING BACK TO U,V,W COORD SYSTEM
1820 HE=ABS(EH/COS(AR))
1830 HU=ABS(HE*COS(AB-AR))
1840 HF=ABS(HE*SIN(AB-AR))
1850 IF HG=0 THEN SG=-C1 ELSE 1870
1860 GOTO 1880
```

```
1870 SG=-90*DR+CI+ATN(MF/MG)   'NEW VALUE OF SIGMA
1880 MD=SQR(MF[2+MG[2)
1890 CLS
1900 MV=ABS(MD*SIN(SG))
1910 IF MV=0 THEN ZT=90*DR ELSE 1930
1920 GOTO 1940
1930 ZT=ATN(MU/MV)    'NEW VALUE OF ZETA
1940 'LPRINT"SG(";N;")/DR =";SG/DR;
1950 'LPRINT"    ZT(";N;")/DR =";ZT/DR
1960 'LPRINT"ATN(MF/MG)/DR: ";ATN(MF/MG)/DR
1970 'LPRINT"MG,ME,MU,MF,MD,MV: ";MG;ME;MU;MF;MD;MV
1980 'LPRINT
1990 PRINT@840,"PROGRAM IS RUNNING, SO WAIT AWHILE!"
2000 IFN>1.5 THEN 2110
2010 U1=U
2020 V1=V
2030 W1=W
2040 U0=U
2050 V0=V
2060 W0=W
2070 N=2
2080 DW(N)=0:DV(N)=0   'OFFSETS ON DML ARE ZERO
2090 HI=1/1.49   'NEW INDEX OF REFRACTION ACRYLIC TO AIR
2100 GOTO 840
2110 U2=U
2120 V2=V
2130 W2=W
2140 DL(M)=SG-TH-EC    'ANGULAR DEVIATION IN THE V-W PLANE
2150 DZ(M)=ATN(TAN(ZT)*SIN(SG)/COS(EC))-AC    'ANGULAR DEVIATION IN THE U-V PLANE
2160 'LPRINT"M,DL(M),DZ(M): ";M;DL(M);DZ(M)
2170 ON M GOTO 2180,2220,2290
2180 UE=XE-1.26    'RIGHT EYE
2190 M=2
2200 'GOTO 2100
2210 GOTO 750
2220 IF AZ=0 THEN 2260
2230 UE=XE+1.26.   'LEFT EYE
2240 M=3
2250 GOTO 750
2260 DZ(3)=-DZ(2)
2270 DL(3)=DL(2)
2280 M=3
2290 FOR I=1 TO 3
2300 DZ(I)=INT(DZ(I)*1000000)/1000     'CONVERTING TO MRAD
2310 DL(I)=INT(DL(I)*1000000)/1000
2320 NEXT I
2330 C5=C5+1
2340 DZ=DZ(3)-DZ(2):DL=DL(2)-DL(3)
2350 Y(1,C5)=AZ:Y(2,C5)=EL:Y(3,C5)=DZ(1):Y(4,C5)=DL(1):Y(5,C5)=DZ:Y(6,C5)=DL
2360 LPRINTTAB(5)AZ;TAB(25)EL;TAB(45)DZ(1);TAB(65)DL(1);TAB(85)DZ;TAB(105)DL
2370 IF ABS(DL)>ABS(FL)THEN FL=DL
2380 IF ABS(DZ)>ABS(FZ)THEN FZ=DZ
2390 IF AZ<=15 AND EL<=5 AND EL>=-15 THEN2400 ELSE 2410
2400 FP=FL:FQ=FZ
2410 'NEXT EL
2420 'LPRINT"-------------":LPRINT
2430 NEXTAZ
2440 LPRINT"-----------"      ":LPRINT:LPRINT
2450 NEXT EL
2460 LPRINT:LPRINT"W/S MAXIMUM VALUE OF VERTICAL BINOCULAR DEVIATION= ";FL
2470 LPRINT"W/S MAXIMUM VALUE OF HORIZONTAL BINOCULAR DEVIATION= ";FZ
2480 LPRINT:LPRINT"HUD MAXIMUM VALUE OF VERTICAL BINOCULAR DEVIATION= ";FP:LPRINT"HUD MAXIMUM VALUE OF
     HORIZONTAL BINOCULAR DEVIA
2490 LPRINT:LPRINT:LPRINT:LPRINT:LPRINT
2500 FQ=0:FP=0:FL=0:FZ=0'    :NEXT DV
2510 PRINT@650,"PROGRAM COMPLETION"
2520 FOR I=1 TO 12:LPRINTCHR$(7);:NEXTI
2530 PRINT"                CREATING VISICALC FILE--TYPE CONT TO CONTINUE"
2540 STOP
2530 PRINT"                CREATING VISICALC FILE--TYPE CONT TO CONTINUE"
2540 STOP
2550 GOTO 2710
2560 '
2570 PRINT"     TEST CASE TO CHECK VC OPTION
2580 DIM Y(6,10)
2590 CLS
2600 A=1
2610 C5=10
2620 FOR N=1 TO 6
2630 FOR M=1 TO 10
2640 Y(N,M)=A
2650 PRINT @ 520, A
2660 PRINT @ 550,M
2670 PRINT @ 570,N
2680 A=A+1
2690 NEXT M
2700 NEXT N
2710 INPUT "NAME OF FILE TO BE USED (8 CHAR. MAX - NO EXTENSION)";UW$
2720 UW$=UW$+"/DIF"
2730 OPEN "O",1,UW$
2740 GR$=CHR$(13)
2750 P$="ABCDEFGHIJKLMNOPQRSTUVWXYZABCDEFGHIJK"
2760 FOR D=C5 TO 1 STEP -1
2770 FOR C=6 TO 1 STEP -1
2780 F=LEN(STR$(D+1))-1
2790 C$=MID$(P$,C,1)
```

```
2800 IF C>26 THEN C$="A"+C$
2810 IF Y(C,D)<0 THEN PRINT#1, ">";C$;RIGHT$(STR$(D+1),F);":";STR$(Y(C,D));GR$;:GOTO 2830
2820 E=LEN(STR$(Y(C;D)))-1:PRINT#1, ">";C$;RIGHT$(STR$(D+1),F);":";RIGHT$(STR$(Y(C,D)),E);GR$;
2830 PRINT @820,Y(C,D);@840,C;@860,D
2840 NEXT C
2850 NEXT D
2860 PRINT#1, ">";"A1";":";CHR$(34);UW$,GR$;
2870 PRINT#1,"/W1";GR$;"/GOC";GR$;"/GRA";GR$;"/GFR";GR$;"/GC9";GR$;"/X>A1:>A1:";GR$;CHR$(00);CHR$(00)
2880 PRINT"    PROGRAM COMPLETION"
2890 CLOSE
2900 FOR PW=1 TO 8
2910 LPRINT CHR$(7);
2920 NEXT
2930 END
2940 '
2950 '
2960 '
2970 '          CONVERTING ROUTING FOR SAABJAB W/S
2980 T=23.56
2990 C=1/25.4
3000 RD=3.1415/180
3010 T1=COS(T*RD)
3020 T2=SIN(T*RD)
3030 INPUT"  TYPE IN U,V,& W COORDINATES (MM):";U,V,W
3040 X=U
3050 Y=V*T1+W*T2
3060 Z=W*T1-V*T2
3070 LPRINT"   VALUE OF U,V,W (MM): ";U,V,W
3080 LPRINT"      VALUE OF X,Y,Z (MM) :"
3090 LPRINTTAB(10)X;TAB(20)Y;TAB(30)Z
3100 LPRINT"      VALUE OF X,Y,Z (INCH) :"
3110 X=X*C:Y=Y*C:Z=Z*C
3120 LPRINTTAB(10)X;TAB(20)Y;TAB(30)Z
3130 LPRINT
3140 GOTO2970
3150 END
```

I claim:

1. A contoured transparency providing low optical distortion of light passing through any portion of it and received at an adjacent, fixed low distortion location, the transparency comprising a sheet of transparent material formed to have a selected contour with a concave side and a convex side each portion of the sheet having a single degree of curvature corresponding substantially to the shape of a cylinder or cone, wherein the sheet has two orthogonal axes across its surface and a thickness that varies along both such axes in a prescribed fashion, such that light passing obliquely through any portion of the sheet at non-perpendicular horizontal and vertical impingement angles and received at a particular fixed low distortion location in the space adjacent to the sheet's concave side is substantially undistorted.

2. A contoured transparency as defined in claim 1, wherein:

the low distortion location is a single point in the space adjacent to the sheet's concave side; and the thickness of the sheet varies in such a way that light passing obliquely through the sheet and impinging on the low distortion location follows a path after exiting the sheet that is substantially parallel with the path it follows before entering the sheet.

3. A contoured transparency as defined in claim 2, wherein:

the sheet has a contour that substantially follows that of a cylinder or cone, said contour having a geometric axis; and the low distortion location is displaced from the sheet's geometric axis.

4. A contoured transparency as defined in claim 3, wherein the low distortion location is located between the sheet's geometric axis and the sheet's concave side.

5. A contoured transparency as defined in claim 2, wherein the sheet's thickness increases as a function of distance from the low distortion location.

6. A contoured transparency as defined in claim 1, wherein the sheet has a contour with a single degree of curvature.

7. A contoured transparency as defined in claim 1, wherein:

a person's head is located at the low distortion location and the lines of sight from the person's two eyes to an object located on the opposite side of the sheet pass obliquely through the sheet; and the thickness of the sheet varies in such a way that any angle between the lines of sight from person's two eyes is the same before and afer passing through the sheet, whereby the two eyes provide images of the object that are superimposed on each other and the person perceives the object to be at a distance substantially equal to its actual distance.

8. A contoured transparency as defined in claim 7, wherein:

the sheet has a contour that substantially follows that of a cylinder or cone, said contour having a geometric axis; and the low distortion location is displaced from the sheet's geometric axis.

9. A contoured transparency as defined in claim 8, wherein the low distortion location is located between the sheet's geometric axis and the sheet's concave side.

10. A contoured transparency as defined in claim 9, wherein the sheet's thickness decreases as a function of distance from the low distortion location.

11. A contoured transparency as defined in claim 7, wherein the thickness of the sheet varies in such a way that both any horizontal angle and any vertical angle between the lines of sight from the person's two eyes are the same before and after passing through the sheet.

12. A method for producing a contoured transparency that provides low optical distortion, comprising steps of:

providing a sheet of transparent material having two orthogonal axes and a substantially uniform thickness;

modifying the sheet to have a prescribed non-uniform thickness across its entire surface, along both orthogonal axes; and forming the sheet into a selected contour with a concave side and a convex side, each portion of the sheet then having a single degree of curvature corresponding substantially to the shape of a cylinder or cone;

wherein the modified sheet's non-uniform thickness is selected such that light passing obliquely through any portion of the sheet at non-perpendicular horizontal and vertical impingement angles and received at a particular fixed low distortion location in the space adjacent to the sheet's concave side follows a path after exiting the sheet that is substantially parallel with the path it follows before entering the sheet.

13. A method as defined in claim 12, wherein:

the step of forming forms the modified sheet into a contour that substantially follows that of a cylinder or cone, said contour then having a geometric axis; and the low distortion location is displaced from the sheet's geometric axis.

14. A method as defined in claim 13, wherein:

the low distortion location is located between the sheet's geometric axis and the sheet's concave side; and the step of modifying modifies the sheet's thickness such that it decreases as a function of distance from the low distortion location.

15. A method as defined in claim 12, wherein the step of modifying includes steps of:

mounting the unmodified sheet on a grinding chuck having a contour complementary to the prescribed non-uniform thickness for the sheet; and grinding flat the exposed side of the sheet mounted on the grinding chuck.

16. A method as defined in claim 12, wherein the steps of modifying and forming are performed separately and the step of forming is performed after the step of modifying.

17. A method as defined in claim 12, wherein the steps of modifying and forming are performed separately and the step of modifying is performed after the step of forming.

18. A method as defined in claim 12, wherein the step of forming forms the sheet into a contour with a single degree of curvature.

19. A contoured transparency providing low optical distortion of light passing through any portion of it and received at an adjacent, fixed low distortion point, the transparency comprising a sheet of transparent material formed to have a contour that substantially follows that of a cylinder or cone, having a geometric axis with a concave surface and a convex surface, wherein the sheet has two orthogonal axes across its surface and a thickness that varies along both such axes in a prescribed fashion, such that light passing obliquely through any portion of the sheet at non-perpendicular horizontal and vertical impingement angles and received at a particular fixed low distortion point adjacent to the sheet's concave surface follows a path after exiting the sheet that is substantially parallel with the path it follows before entering the sheet.

20. A contoured transparency as defined in claim 19, wherein:

the fixed low distortion point is located between the sheet's geometric axis and the sheet's concave surface; and the sheet's thickness increases as a function of distance along the two orthogonal axes from the portion of the sheet nearest the low distortion point.

21. A contoured transparency providing minimal binocular deviation for light received from a distant object, comprising a sheet of transparent material formed to have a selected contour with a concave surface and a convex surface, each portion of the sheet having a single degree of curvature corresponding substantially to the shape of a cylinder or cone, wherein the sheet is positioned such that a person's head is located at a particular fixed low distortion location adjacent to the sheet's concave surface, wherein the person's two eyes receive light from a distant object after passing through the sheet at non-perpendicular horizontal and vertical angles of impingement, and wherein the sheet has two orthogonal axes across its surface and a thickness that varies along both such axes in a prescribed fashion, such that any horizontal and vertical angles between the lines of sight from the person's two eyes are substantially the same before and after passing through the sheet, whereby the images of the object produced by the person's two eyes are superimposed on each other and eyestrain is minimized.

22. A contoured transparency as defined in claim 21, wherein:

the sheet has a contour that substantially follows that of a single cylinder or cone having a geometric axis;

the low distortion location is located between the sheet's geometric axis and the sheet's concave surface; and the sheet's thickness decreases as a function of distance along the two orthogonal axes from the point on the sheet nearest the low distortion location.

* * * * *